(12) United States Patent
Beaton et al.

(10) Patent No.: US 9,985,334 B2
(45) Date of Patent: May 29, 2018

(54) ANTENNA MANDREL WITH MULTIPLE ANTENNAS

(71) Applicant: Johnson & Johnson Vision Care, Inc., Jacksonville, FL (US)

(72) Inventors: Stephen R. Beaton, Jacksonville, FL (US); Michael D. Ferran, Jacksonville, FL (US); Dawn Jamisha Owens, Jacksonville, FL (US); Randall B. Pugh, St. Johns, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 233 days.

(21) Appl. No.: 14/918,940

(22) Filed: Oct. 21, 2015

(65) Prior Publication Data

US 2017/0115511 A1    Apr. 27, 2017

(51) Int. Cl.
*H01Q 1/22* (2006.01)
*H01Q 7/00* (2006.01)
*G02C 11/00* (2006.01)
*G02C 7/04* (2006.01)

(52) U.S. Cl.
CPC .......... *H01Q 1/2208* (2013.01); *G02C 7/049* (2013.01); *G02C 11/10* (2013.01); *H01Q 7/00* (2013.01)

(58) Field of Classification Search
CPC ...... H01Q 1/22; H01Q 1/2208; H01Q 1/2216; H01Q 1/2225; G02C 7/04; G02C 7/049; G02C 11/10
USPC ............. 351/159.01, 159.02, 159.03, 159.69
See application file for complete search history.

(56) References Cited

U.S. PATENT DOCUMENTS

| | | | |
|---|---|---|---|
| 5,383,912 A | 1/1995 | Cox | |
| 9,101,309 B1 | 8/2015 | Liu et al. | |
| 9,459,469 B2* | 10/2016 | Markus | G02C 7/04 |
| 2010/0308939 A1 | 12/2010 | Kurs | |
| 2011/0022411 A1 | 1/2011 | Hjelm | |
| 2011/0160853 A1 | 6/2011 | Scholten | |
| 2012/0161767 A1 | 6/2012 | Hardy | |
| 2013/0194540 A1* | 8/2013 | Pugh | H01Q 1/22 351/159.03 |
| 2014/0277291 A1 | 9/2014 | Pugh et al. | |
| 2014/0312834 A1 | 10/2014 | Tanabe | |
| 2014/0340631 A1 | 11/2014 | Pugh | |
| 2016/0223842 A1 | 8/2016 | Yun et al. | |

FOREIGN PATENT DOCUMENTS

| | | |
|---|---|---|
| EP | 2282412 A1 | 2/2011 |
| WO | WO2015003537 A1 | 1/2015 |

OTHER PUBLICATIONS

Chen L. et al., Energy harvesting system integrated on wearable contact lens. *2015 IEEE International Symposium on Antennas and Propagation & USNC/URSI National Radio Science Meeting*, Jul. 24, 2015, pp. 358-359. (abstract provided).

* cited by examiner

*Primary Examiner* — Robert Karacsony

(57) ABSTRACT

Antennas and antenna mandrels or assemblies may be designed and configured to enable one of one- or two-way communication and/or power transfer with mechanical devices such as ophthalmic devices, including contact lenses. These antennas and antenna mandrels or assemblies may be utilized to transmit data from the mechanical devices to receive data from a transmitter, and/or inductively charge an electromechanical cell or the like incorporated into a mechanical device.

56 Claims, 8 Drawing Sheets

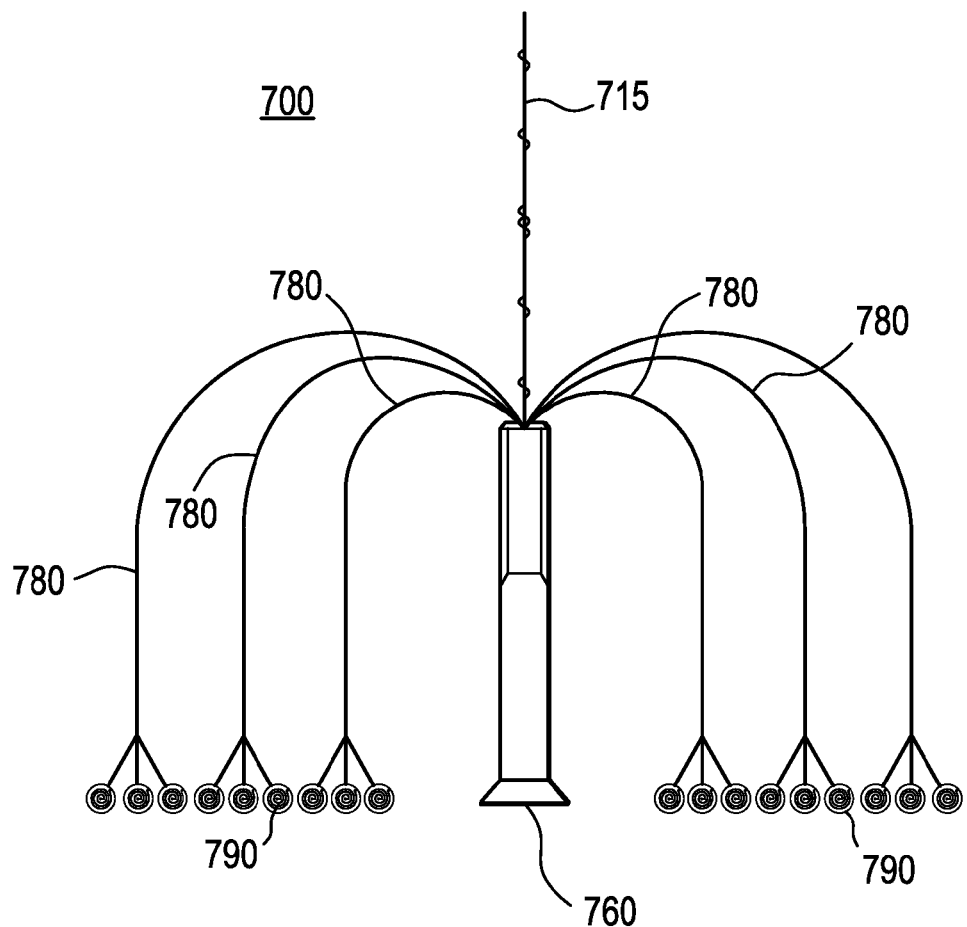
FIG. 7
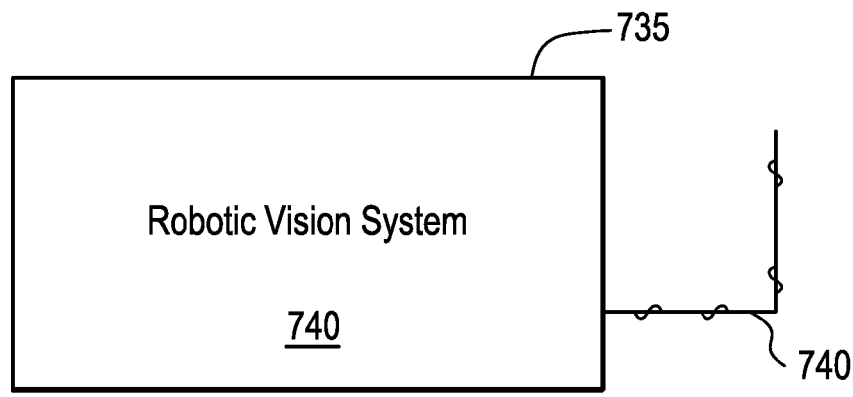

ANTENNA MANDREL WITH MULTIPLE ANTENNAS

BACKGROUND OF THE INVENTION

1. Field of the Invention

The present invention relates to a device that includes an array of small antennas on a mandrel capable of interfacing with biomedical devices, and more particularly ophthalmic devices, such as wearable lenses, including contact lenses, implantable lenses, including intraocular lenses (IOLs) and any other type of device comprising optical components that incorporate electronic circuits and associated antennas/antenna assemblies to enable one of one- or two-way communication with the one or more electronic components and/or power transfer.

2. Discussion of the Related Art

As electronic devices continue to be miniaturized, it is becoming increasingly more likely to create wearable or embeddable microelectronic devices for a variety of uses. Such uses include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to correct refractive errors and/or augment or enhance performance of the eye. In another example, either with or without adjustable focus, a wearable contact lens may incorporate electronic sensors to detect concentrations of particular chemicals in the precorneal (tear) film.

The use of embedded electronics in a lens introduces a potential requirement for communication with the electronics, for a method and device for powering and/or re-energizing the electronics, for interconnecting the electronics, for internal and external sensing and/or monitoring, and for control of the electronics and the overall function of the lens.

Often it is desirable to provide for communication to or from the embedded electronics for the purpose of control and/or data gathering. Communication of this nature should preferably be performed without direct physical connection to the lens electronics, such that the electronics may be fully sealed and to facilitate communication while the lens is in use. Hence it is desirable to couple signals to the lens electronics using near-field communication technology. Accordingly, there exists a need for an antenna structure appropriate for short-range wireless communication and capable of communicating with an optical lens assembly containing an antenna such as a soft contact lens.

Near-field communication (NFC) provides short range wireless connectivity that carry secure two-way interactions between electronic components. NFC enables communication over short distance through either inductive or capacitive coupling. This means that oscillating electric and magnetic fields are separate and power may be transferred via electric fields by capacitive coupling (electrostatic induction) between metal electrodes or via magnetic fields by inductive coupling between coils of wire. In capacitive coupling, the power is transmitted by electric fields between electrodes such as metal plates. The transmitter and receiver electrodes form a capacitor, with the intervening space as the dielectric. An alternating voltage generated by the transmitter is applied to the transmitting plate, and the oscillating electric field induces an alternating potential on the receiver plate, which allows power to be transferred. Capacitive coupling is not traditionally used in low-power applications such as the present invention because the high voltages on the electrodes required to transmit significant power may potentially be hazardous. Additionally, electric fields interact strongly with most materials, including the human body, and may possibly cause excessive electromagnetic field exposure. In inductive coupling, power is transferred between coils of wire by a magnetic field. The transmitter and receiver coils together form a transformer. The magnetic field passes through the receiving coil, which facilitates the transfer of energy from one circuit to another via the mutual inductance between the two circuits. The power transferred increases with frequency and the mutual inductance between the two coils, which depend on their geometry and the distance between them.

Antenna efficiency on-body is degraded for predominantly electric-field or "E-field" antennas. Thus, the most acceptable method of communicating and recharging a battery on-body is through inductive coupling, whereby the coil(s) of the external antenna are magnetically coupled to an antenna embedded in the ophthalmic device. With the existence of inductive structures such as antennas, antenna assemblies and/or coils appropriate for use in an optical assembly, it is desirable to provide a device that utilizes a convenient method for aligning the coil structure with an inductive coil structure for efficient near field coupling.

Embedding electronics and communication capabilities in a contact lens presents a number of general challenges. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters (assuming a lens with a 7 mm radius) of the transparent polymer forming the lens while protecting components from the liquid environment on the eye. It may also difficult to make a contact lens comfortable and safe for the wearer with the added thickness of additional components.

With respect to communication devices, specific challenges include limited antenna efficiency, which is directly related to the size or area for a coil antenna, and the number of coil turns. Although, the limit of miniaturization of electronic devices has yet to be determined, the sizes of some elements in electronics remain constrained by the rules of physics, and cannot match the miniaturization demonstrated by circuit elements. Antennas needed to radiate information remain relatively large with respect to electronics the size of a grain of salt. The size of the antenna relates to the maximum inductance achievable and the maximum voltage or current that may be transferred to the device, and differential sizing has the potential to delay or exacerbate the ability to coarse-align and fine-tune align antennas to initiate a communication link. The primary issue is that, if any antenna is small enough to include on a circuit embedded in an ophthalmic device, it may not provide sufficient power levels. The received power at the antenna must be of sufficient strength to allow for transformation to adequate supply voltage levels for the circuitry inside the ophthalmic device, when excited by a reasonable power level from an external device. The efficiency of the power transfer between the antenna coil inside the ophthalmic device and an external antenna is proportional to the operating frequency, the number of windings, the angle and the size of the two coils relative to each other, and the distance between the two coils. In some cases it may not be desirable to simply increase the power applied to the external antenna or to alter the size or number of turns. A larger size ratio between the two antennas could result in non-predictable or performance-degrading characteristics. It may be better to closely couple an equally sized, low-power external antenna. However, considering the fundamental size constraints of the internal antenna, equally sized antennas would cause the antenna coils to be extremely sensitive to alignment. Even the slightest mis-alignment of the coils may result in insufficient power. Moreover, this difficulty increases greatly when utilizing micron-sized antennas, where one antenna is embedded inside an ophthalmic device, which eliminates the possibility of any direct contact coupling methods.

Accordingly, there exists a need for providing a mechanically robust external antenna assembly that meets the requirements for functionality and performance in the volume and area of a contact lens.

SUMMARY OF THE INVENTION

The antennas and/or antenna assemblies of the present invention overcome the disadvantages as briefly set forth above.

The present invention relates to a device that enables communication between an ophthalmic lens assembly containing a radiation element and a physical object. The device may be utilized to enable radio frequency for reading and programming data, serial number identification, power transfer, tracking and management. More specifically the present invention relates to methods and means of wirelessly connecting internal antenna arrangements in ophthalmic devices to external radiation elements so as to propagate their radio waves. The device preferably provides a quick and convenient method to couple electromagnetic energy from circuit elements with built-in antennas embedded in an ophthalmic lens, for example, a contact lens so that it may be used as a mechanism for collecting medical data, transmitting information or data to a medical administrator or manufacturer for assessment, or more generally speaking a method for utilizing near field communication technologies.

The present invention utilizes inductive coupling to convey electrical signals and/or energy from a circuit on one substrate to an antenna on another substrate, much like a transformer. The secondary side of the transformer is located on the circuit carrier inside of the ophthalmic device and the primary side on the antenna mandrel/antenna assembly.

In accordance with a first aspect, the present invention is directed to an ophthalmic lens assembly. The ophthalmic lens assembly comprises a lens configured for placement in at least one of the inside and proximate to a surface of an eye, the lens including an optic zone configurable for at least one of vision correction and vision enhancement, and at least one antenna arrangement operatively associated with the one or more electronic components for providing at least one of one or two way communication with the one or more electronic components and power transfer. The antenna or antenna assembly incorporated into mechanical devices such as ophthalmic devices may function much like the secondary side of the transformer, which produces the means for one and/or two way communication, and a means of powering the electronics or recharging a power storage device. The antenna mandrel/antenna assembly of the present invention may be utilized to inductively couple the antennas on the device to the antenna embedded in an ophthalmic device to convey electrical signals and energy.

An exemplary antenna mandrel/antenna array in accordance with the present invention may comprise one or more submillimeter-sized antenna structures, a three-dimensional substrate, a circuit board, an electronic circuit, an active switch and a support structure. The antenna may include a coil comprising one or more loops of wire to create an antenna with a coil diameter that may range from about 0.5 mm to about 3 mm. The antenna array may comprise a matrix of isolated submillimeter-sized antennas with varying angular and radial positions aligning with the peripheral and/or skirt zone of a lens structure. In some exemplary embodiments, the antenna structures may be embedded in a three-dimensional substrate such as a thin flexible polymer, flexible metallized polyimide film, metallized flexible ceramic films, flexible thin silicon- or silica-based substrates, polytetrafluoroethylene (PTFE), liquid crystal polymer (LCPS) or any other accommodating materials suitable for housing a matrix of antennas without impacting an ophthalmic device. In alternate exemplary embodiments, the antenna or the antenna structure may be attached or affixed to an electrical wire. The electronic circuit may comprise a number of electronic components mounted on the circuit board, and the circuit board may provide wiring traces to interconnect the electronic components. An active switching mechanism may be utilized to activate individual antennas within the antenna structure, and to alternate between the calibration mode, receiving mode, and charging mode.

Antennas and antenna mandrels/assemblies used in inductive systems, such as in the present invention preferably utilize mutual inductance so that the coils are magnetically linked together by a common magnetic flux. The amount of mutual inductance that links one coil to another depends very much on the relative position of the two coils. If one coil is positioned next to the other coil so that their physical distance is very small and they are axially aligned, then nearly all of the magnetic flux generated by the first coil will interact with the coil turns of the second coil inducing a relatively large electromagnetic field ("emf") and therefore producing a large mutual inductance value. As previously stated, the power transferred increases with the mutual inductance between the two coils, and that value is dependent on the distance between the coils. For instance, if the two coils are farther apart from each other or at different angles, the amount of induced magnetic flux from the first coil to the second will be weaker, producing a much smaller induced emf and a much smaller mutual inductance value.

Due to the fact that there will always be some loss due to leakage and position, magnetic coupling between two coils can never reach or exceed 100 percent. If some of the total magnetic flux links the two coils, the amount of flux linkage can be defined as a fraction of the total possible flux linkage between coils. The fractional value is called the coupling coefficient, k, and is generally expressed as a decimal number between 0 and 1 instead of a percentage. The coupling coefficient is dependent upon the geometry of the coils, and their relative positions. Obviously, k=0 at large distances separating the coils, and can approach the limit of 1 for exceptionally strong coupling, where the magnetic flux fully links both coils.

Due to the miniaturization of the components the expected range of k is $0 \leq k \leq 0.002$, however k may be maximized utilizing the following relationship, $$k \leq \left(\frac{r_{small}}{r_{large}}\right)^2, \quad (1)$$

where $r_{small}$ and $r_{large}$ represent the radii of the antenna coils, and the upper bound for k is based on the area ratio for two co-planar spiral conductors aligned about their center. Additionally, the limited space within an ophthalmic device restricts both radii from exceeding submillimeter-sized ranges to maximize the coupling coefficient. Therefore, a relatively small misalignment of the coils causes the coupling coefficient to change. Even a 0.2 mm misalignment of the coils could then result in insufficient power to the secondary coil because more of the magnetic field from the first coil misses the second coil. Higher efficiencies may be achieved if the coils are closer together, and the coils' axes are aligned. To overcome this limitation and enable higher power transfer, the present invention mimics the shape of the lens structure so that the antennas are closer together and the coils' axes may be easily coarse-aligned. The antennas occupy an area of approximately 40 square millimeters. This area has an inner diameter of 7 millimeters and an outer diameter of 10 millimeters, and is configured to interface with an antenna on the concave or convex side of the lens. Geometrically matching the antenna structure to the lens, and concentrating the antennas on the substrate within the aforementioned area, may reduce the complexity of trying to coarse-align micron-sized antennas to initiate coupling. The antenna mandrel may be coarse-aligned with the lens structure, so that multiple antennas on the mandrel may be positioned closely to the same region as the antenna embedded in the ophthalmic device. In some embodiments, the present invention may comprise a robotic vision system to facilitate and expedite the coarse-alignment and the fine-tune alignment process. For example, the robotic vision system may be configured to move or rotate about one or more of the planes in three-dimensional space, in order to locate the submillimeter-sized antenna embedded in the ophthalmic device. In another embodiment, the robotic vision system may be fixed and connected to a moveable base that rotates or moves about one or more planes in three-dimensional space to allow a vision system to fully scan the ophthalmic device for the submillimeter-sized antenna. Once the antennas have been coarse aligned, fine-tuning or final alignment may be quickly completed by making small adjustments to the orientation of the mandrel via electrical or mechanical movements or rotations about one or more planes in three-dimensional space. Electronically interrogating the matrix of antennas on the antenna mandrel through a controller and/or the ability search the ophthalmic device for the submillimeter-sized antenna may expedite the communication process.

Antennas and antenna mandrels/assemblies designed for medical devices such as ophthalmic devices may be utilized or configured for a wide variety of applications. Applications include transmitting/receiving data to/from the ophthalmic device, sensing information from the environment in which the ophthalmic device is placed, charging batteries or other power sources associated with the ophthalmic device and actuation or activation of other devices. Data flow to and from the ophthalmic devices may include communication with key fobs, smart phones or other hand-held devices and wireless networks, cases for holding the ophthalmic devices, e.g. cleaning cases for contact lenses that utilize chemical or UV based disinfection systems, as well as any other types of devices capable of receiving text information, video information, telemetry information, graphics, software, or code for reprogramming or updating, and the like via RF or inductive wireless link. The data or information to be transmitted or received may include tear film analysis, intra-ocular pressure, heart rate, blood pressure and the like. The ophthalmic device may be utilized to sense any number of parameters depending on the device application, for example, ciliary muscle contraction for an accommodating lens. Relatedly, the output from the antenna or antenna system may be utilized to actuate or activate secondary devices for changing the optics of the device and/or to dispense drugs and/or therapeutic agents. The antennas and antenna assemblies may be utilized, as stated above, to recharge batteries or for continuous powering from a remote source. This may be in the form of inductive powering rather than charging. The antennas may also be utilized to communicate between ophthalmic devices, such as lenses, to detect eye convergence during reading or to synchronize behavior for three-dimensional holographic realization.

The antennas and antenna mandrels/assemblies may be physically realized in any number of ways. Physical realizations include conductive traces on a circuit incorporated in a device, and/or turns or wire embedded in three-dimensional substrate conductive traces printed in/on the device, and/or as a layer in a stacked die assembly.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 7 illustrates a planar view of an alternative exemplary three-dimensional antenna mandrel.

DETAILED DESCRIPTION OF THE PREFERRED EMBODIMENTS

Figure 1A:
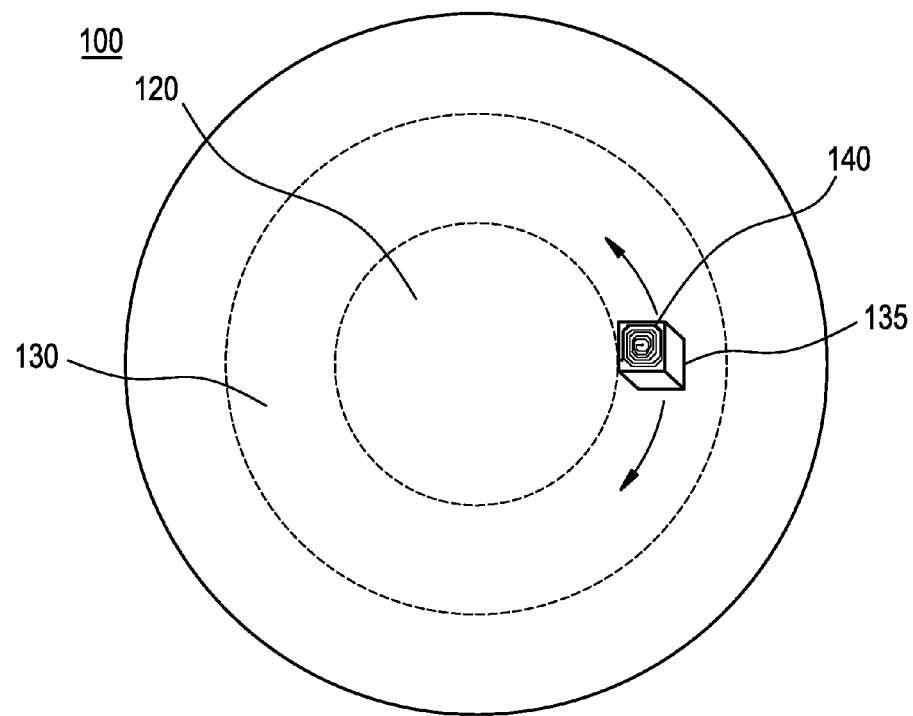
FIG. 1A is a planar view of an ophthalmic device containing miniaturized circuit elements with a built-in antenna.

Referring to FIG. 1A, there is illustrated a first exemplary embodiment of an ophthalmic device 100. Although illustrated as a contact lens, it is important to note that the present invention may be utilized in conjunction with any number of devices having medical and ophthalmic applications as well as any devices incorporating lenses, such as cameras, binoculars and microscopes. The exemplary ophthalmic device 100 comprises a circuit element 135 with built-in submillimeter-sized antenna 140 positioned outside of the optic zone 120 in the peripheral zone 130. As utilized herein, the circuit element 135 may comprise one or more electric components embedded on any suitable substrate, including copper traces on a polyimide, aluminum or copper on silicon oxide or silicon nitride, or other conductors on insulators. Circuit element 135 may be configured with the necessary electrical components to execute any number of applications for the ophthalmic device. The antenna 140 may be formed from any number of suitable conductive materials and constructed utilizing any number of techniques. In other exemplary embodiments, the antenna traces may be created directly within the contact lens or an optic insert. The lens molding process may allow for insertion of an antenna or deposition of an antenna within the polymer of the contact lens. An antenna may be deposited as a printed, curable trace during manufacture. An insert, containing the antenna, may be added to the contact lens during molding. An antenna may be fabricated on an optic insert by selectively depositing metal, broadly depositing then selectively removing metal, depositing a liquid curable conductor, or other means.

Figure 1B:
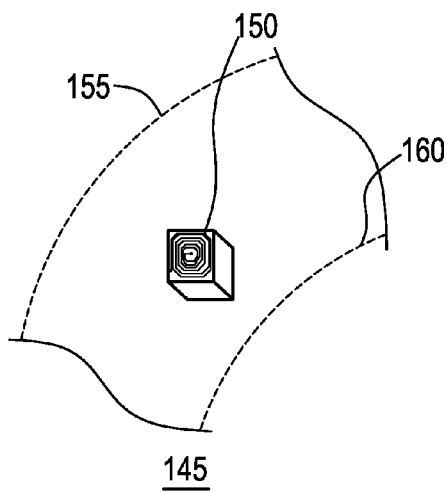
FIG. 1B illustrates the dimensional constraints for the circuit elements within the ophthalmic device.

FIG. 1B illustrates additional details of the preferred area 145 in the peripheral zone 130 of the ophthalmic device 100, which the IC or circuit element with built-in antenna 150 (hereinafter "internal submillimeter-sized antenna") may occupy. The internal submillimeter-sized antenna 140 should be placed in just 40 square millimeters between an area with a 7 mm inner diameter 160 and a 10 mm outer diameter 155. As previously stated, the components to be placed in the lens have to be miniaturized and integrated onto just 1.5 square centimeters (assuming a lens with a 7 millimeter radius) of the transparent polymer.

Figure 1C:
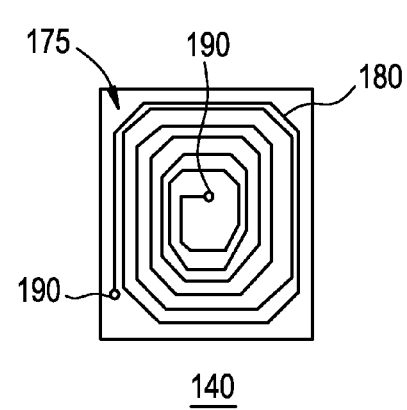
FIG. 1C illustrates the antenna coil on top of the circuit elements embedded in the ophthalmic device.

FIG. 1C illustrates a more detailed view of the exemplary embodiment of the antenna 140. The exemplary antenna 140 comprises one or more interconnects 190 and wiring traces 180 on a substrate 175. The antenna 140 may be formed by one or more turns of wire or conductive traces 180 on top of the miniaturized circuit elements 135 illustrated in FIG. 1A. Embedded on the substrate 175, the antenna 140 is arranged to form an electromagnetic structure having predetermined characteristics for operation as an antenna, such as directivity, efficiency and/or gain when worn in a body or in-eye, or as an inductor for magnetic coupling to another inductor. In some exemplary embodiments, the antenna may comprise a multi-turn loop antenna, a spiral antenna, coil antenna or a single antenna that may be utilized for one or both communication and power transfer. The antenna may be electronically coupled to the electronic circuit. In some exemplary embodiments, the electronic circuit may provide a transmittal signal to the antenna in order to transmit an outgoing electromagnetic signal board on the transmit signal while in alternate exemplary embodiments, the antenna may receive an incoming electromagnetic signal and provide some received signal to the electronic circuit. In yet another alternate exemplary embodiment, the antenna may be utilized to transmit and receive signals. In yet another exemplary embodiment, the antenna may be utilized to inductively charge a storage element or battery. In some exemplary embodiments, a single antenna may also be utilized for both communication and power transfer. As stated above, the antenna may be fabricated from any number of suitable conductive materials and alloys, including copper, aluminum, silver, gold, nickel, indium tin oxide, graphene and platinum. Preferably, the antenna is fabricated from a non-reactive material. The substrate may be formed from any suitable, insulating-material such as silicon, silicon dioxide, silicon nitride, a thin polymer, polyimide film, ceramic, polytetrafluoroethylene(PTFE), liquid crystal polymer (LCPS) or any other accommodating materials suitable for housing an antenna without impacting an ophthalmic device.

Figure 2A:
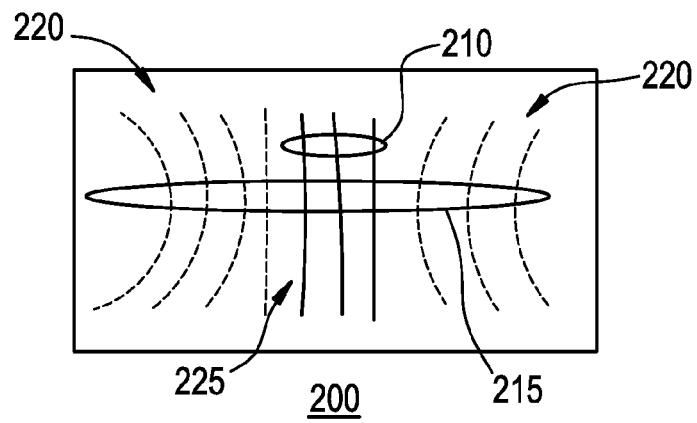
FIG. 2A-2C illustrate the distribution of the magnetic fields between transmitter antenna coils and receiver antenna coils.
Figure 2B:
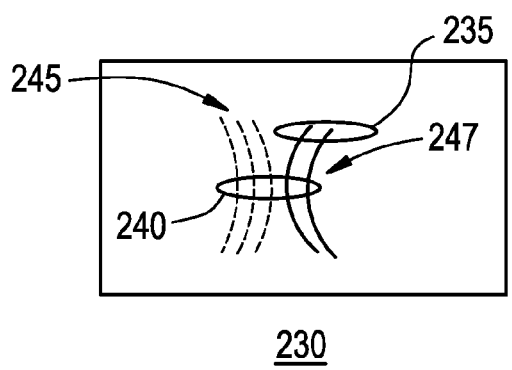
Figure 2C:
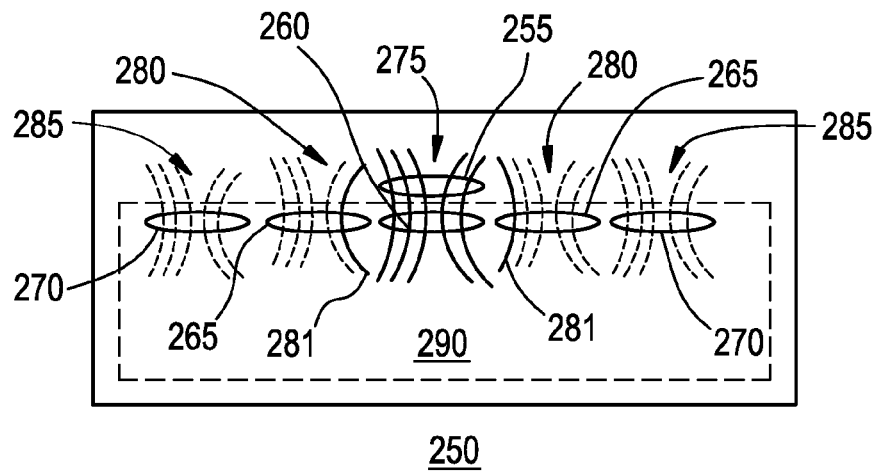

FIGS. 2A-2C illustrate the possible magnetic field distribution between two antenna coils. When the transmitter and receiver coil form a transformer, an alternating current through the transmitter coil creates an oscillating magnetic field which passes through the receiving coil. The magnetic field induces an alternating EMF, which creates an AC current in the receiver. The power transferred between the coils increases with frequency and the mutual inductance between the coils, which depends on the geometry and distance between the coils. The magnetic field lines illustrated demonstrate the distribution situation of the magnetic field, where the solid lines indicate how much of the magnetic field flux is encircled by the receiver, being higher if a high density of the lines are projected through the receiver. Generally, the amount of inductive coupling that exists between two antenna coils is expressed as a decimal number between 0 and 1, where 0 indicates zero or no inductive coupling, and 1 indicating full or maximum inductive coupling. Therefore, when a large amount of the magnetic field lines diverge from the receiver, as illustrated by the dashed magnetic field lines, the coupling between the two coils is reduced causing a reduction in the coupling coefficient value. However, the objective is to increase the coupling coefficient between the two coils because it affects the ability to transfer power and the power transfer efficiency.

Referring now to FIG. 2A, there is illustrated the distribution of the magnetic field 200 between receiver coil antenna ($R_r$) 210, and a larger transmitter coil antenna ($R_t$) 215. As exemplified by the number of solid magnetic field lines 225 projected through the receiver, the ratio of the radii of the two coils ($R_r<<R_t$) may be causing the coils to be loosely coupled. A larger transmitter coil may lead to higher power transfer efficiency, but a lower transfer of power because the amount flux constrained to the desired path of the receiver is minimal, resulting in excessive loss or magnetic field leakage, as illustrated by the dashed field lines 220. Therefore, utilizing a larger coil radius for the transmitter antenna may not improve the coupling coefficient at a fixed distance.

In FIG. 2B, there is illustrated the distribution of the magnetic field 230 between receiver coil antenna ($R_r$) 235 and an equally sized transmitter coil antenna ($R_t$) 240. The number of solid magnetic field lines 247 illustrate the weakness of the coupling coefficient. Although the radii are geometrically equivalent, the coils are not spatially aligned and the reflected impedance from the secondary coil to the primary coil, as illustrated by the dashed field lines 245 is less than the initial impedance of the primary coil because of the reduced coupling coefficient. Therefore, both the transfer efficiency and transfer power will decrease.

Referring now to FIG. 2C, there is illustrated the distribution of the magnetic field 250 between receiver coil antenna ($R_r$) 255 and antenna structure transmitter 290. The antenna structure 290 may comprise a matrix of equally-sized antennas 260, 265 and 270 ($R_t$), concentrically aligned with the lens structure. Therefore, the ratio of the radii of the coils of the antennas on the transmitter antenna structure 290 and the receiver antenna coil 255 are equivalent ($R_r=R_t$). The magnetic field lines 275, 280, and 285 illustrate that the distribution of the magnetic field 250 may vary depending upon the spatial alignment of the two coils. As previously stated, a relatively small misalignment of the coils causes the coupling coefficient to change. The receiver coil antenna 255 and transmitter coil antenna 260, are strongly coupled which indicates that the reflected impedance from the secondary coil to the primary coil is identical to the initial impedance of the primary coil. As exemplified by the number of solid lines 275 projected directly through the receiver, the transfer power may arrive at the maximum value, and transfer efficiency may possibly reach 50%. The distribution of the magnetic field lines between the receiver antenna coil 255 and transmitter coil antennas 265 are not evenly distributed, and the ratio between the solid and dashed magnetic field lines 285 reveal a stronger concentration of magnetic flux density occur only near the edges of the coil closest to the receiver coil (denoted by the solid magnetic field line 281). The transmitter antenna coils 270 are loosely coupled with the receiver antenna coil, as illustrated by dashed magnetic field lines 285.

Looking at FIGS. 2A, 2B and 2C there are some clear differences in the magnetic field distributions. As expected, the coupling coefficient may increase under two conditions: (1) the ratio of radii of the receiver and transmitter antenna coils approach unity; and (2) the primary and secondary coils are axially aligned. As known to those skilled in the art, one potential explanation for the increase could be the magnetic flux distribution is associated with the innermost radius of the windings. The magnetic field intensity of the transmitter coil with the smaller radius may have a higher coupling coefficient because the field lines are radiated directly through the receiver. Whereas the magnetic field distribution of the coil with a relatively large radius decreases evenly and slowly from the periphery to the center increasing the magnetic flux leakage and decreasing the coupling coefficient.

Figure 3A:
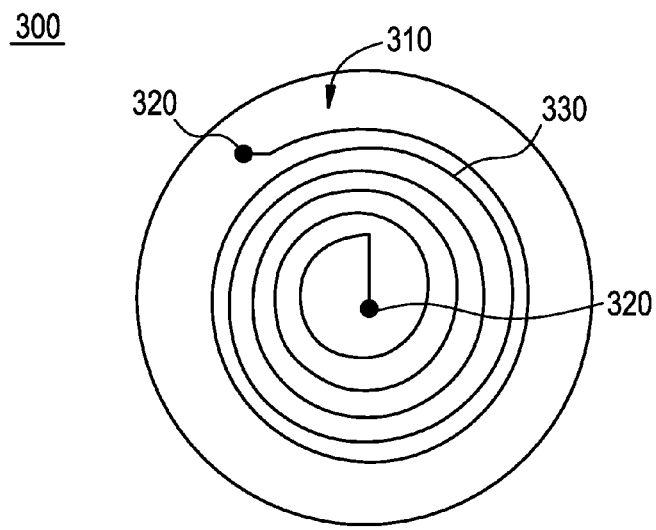
FIG. 3A-3B illustrate an exemplary antenna and planar view of an antenna structure.
Figure 3B:
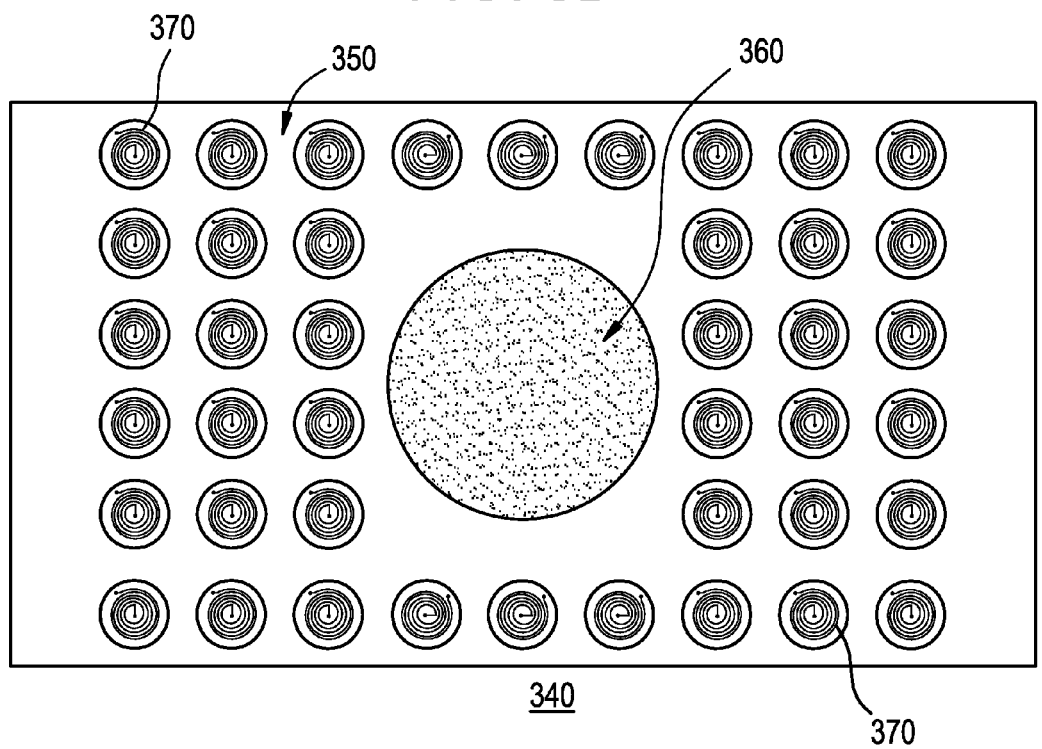

FIG. 3A illustrates an exemplary transmitter antenna coil 300. Transmitter antenna coil 300, as illustrated, comprises one or more electrical interconnects 320 and one or more turns of wire or conductive traces 330 formed on a three-dimensional substrate 310. In FIG. 3B there is illustrated an exemplary planar view of an antenna structure 340 that may be utilized with a radio transmitter or radio transmitter circuit. The antenna structure 340, as illustrated, comprises a matrix of transmitter antenna coils 370 embedded on a three-dimensional substrate 350 in such a manner as to be concentrically aligned with the optic zone 360 of a lens structure.

Embedded on a three-dimensional substrate 310 and 350, the transmitter antenna coils 300 and 370 respectively, are arranged to form an electromagnetic structure having pre-determined characteristics for operation as an antenna, such as directivity, efficiency and/or gain when worn in a body or in-eye, or as an inductor for magnetic coupling to another inductor. As stated above, the antennas 300 and 370 may be fabricated from any number of suitable conductive materials and alloys, including copper, aluminum, silver, gold, nickel, indium tin oxide and platinum. Preferably, each antenna is fabricated from a non-reactive material. The three-dimensional substrates 310 and 350 may include any suitable insulating-material such as silicon, silicon dioxide, silicon nitride, a thin polymer, polyimide film, ceramic, glass, polytetrafluoroethylene (PTFE), liquid crystal polymer (LCPS) or any other accommodating materials suitable for housing an antenna without impacting an ophthalmic device.

The antenna 300 and antenna structure 340 illustrated in FIGS. 3A and 3B respectively may be utilized for any number of suitable applications. Antennas or antenna structures may serve as a means for receiving signals, as a means for transmitting signals, as an inductive coupling means, or any combination thereof. The function of the antenna determines its design as well as it supporting circuitry. For example, an antenna may be coupled to a receiver circuit, a transmitter circuit, an inductive charging circuit or to any combination thereof. Basically, an antenna is an electrical device that converts electromagnetic waveforms into electrical signals, electrical signals into electromagnetic waveforms, or electrical signals into different electrical signals. The discussion below focuses on the different uses of an antenna and its associated circuitry.

Figure 4:
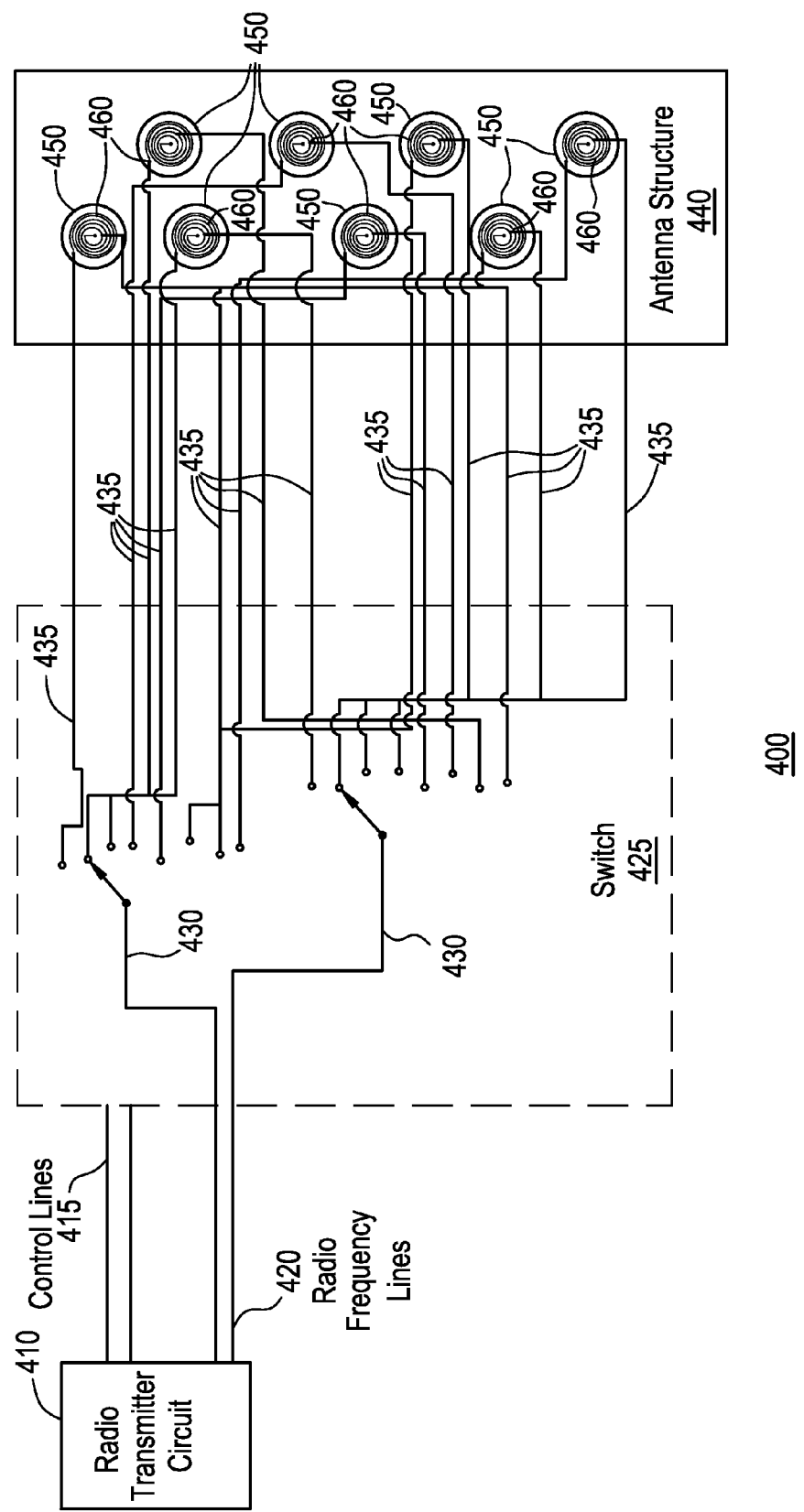
FIG. 4 is a diagrammatic representation of a radio transmitter system incorporating an antenna structure that may be utilized for both communication and power transfer in accordance with the present invention.

FIG. 4 illustrates a radio transmitter system 400 incorporating an antenna structure. The radio transmitter system 400 comprises a radio transmitter circuit 410, one or more control lines 415, one or more radio frequency lines 420, a switch 425, and an antenna structure 440. As known to one of ordinary skill in the art, the radio transmitter system 400 may comprise one or more suitable electrical components necessary to execute various applications, which utilize radio communication technologies. The radio transmitter circuit 410 may be designed to wirelessly transfer data or power to an ophthalmic device. For example, if the radio transmitter system 400 is configured to transfer data, the radio transmitter circuit 410 may comprise an antenna match circuit, a transmitter circuit, a controller, a battery, power management circuit and a sensor. In this exemplary embodiment, the switch 425 may be utilized to select the optimal antenna and alternate between calibration and receiving mode. Additionally, the antenna structure 440 may be adapted to receive a matched transmit electrical signal and broadcast or radiate a transmit electromagnetic signal based on the transmit electrical signal. In another exemplary embodiment, the radio transmitter system 400 may be configured to power an ophthalmic device; the radio transmitter circuit 410 may comprise all the standard elements as is known in the art. For this exemplary embodiment the switch 425 may be utilized to select the optimal antenna and to alternate between calibration and charging mode, and the antenna structure 440 may be utilized to create a magnetic field from the system's current.

The radio transmitter circuit 410 may comprise one or more complex electrical circuits depending on what is needed for the particular application. The switch 425 is connected to the radio transmitter circuit 410 via the control lines 415 and the radio frequency lines 420. The switch 425 comprises one or more selective switches 430, which may be utilized to selectively activate an antenna 450 on the antenna structure 440 for the desired application and to alternate between modes (e.g. calibration and charging). The switch controls each antenna 450 on the antenna structure 440 via a conducting cable or an electrical wire 435. The antenna 450 comprises one or more electrical interconnects 460 that connect to the selective switch 430 via the conducting cable or electrical wire 435.

For example, the radio transmitter system 400 may be designed to transfer data to an ophthalmic device with an embedded antenna. The antenna structure 440 may be placed over the convex or concave surface of the ophthalmic device. The antenna structure may be electrically interrogated by the radio transmitter circuit to see which antenna has the highest coupling coefficient to the antenna on the lens. The selected antenna may then be used to communicate with the lens.

Figure 5:
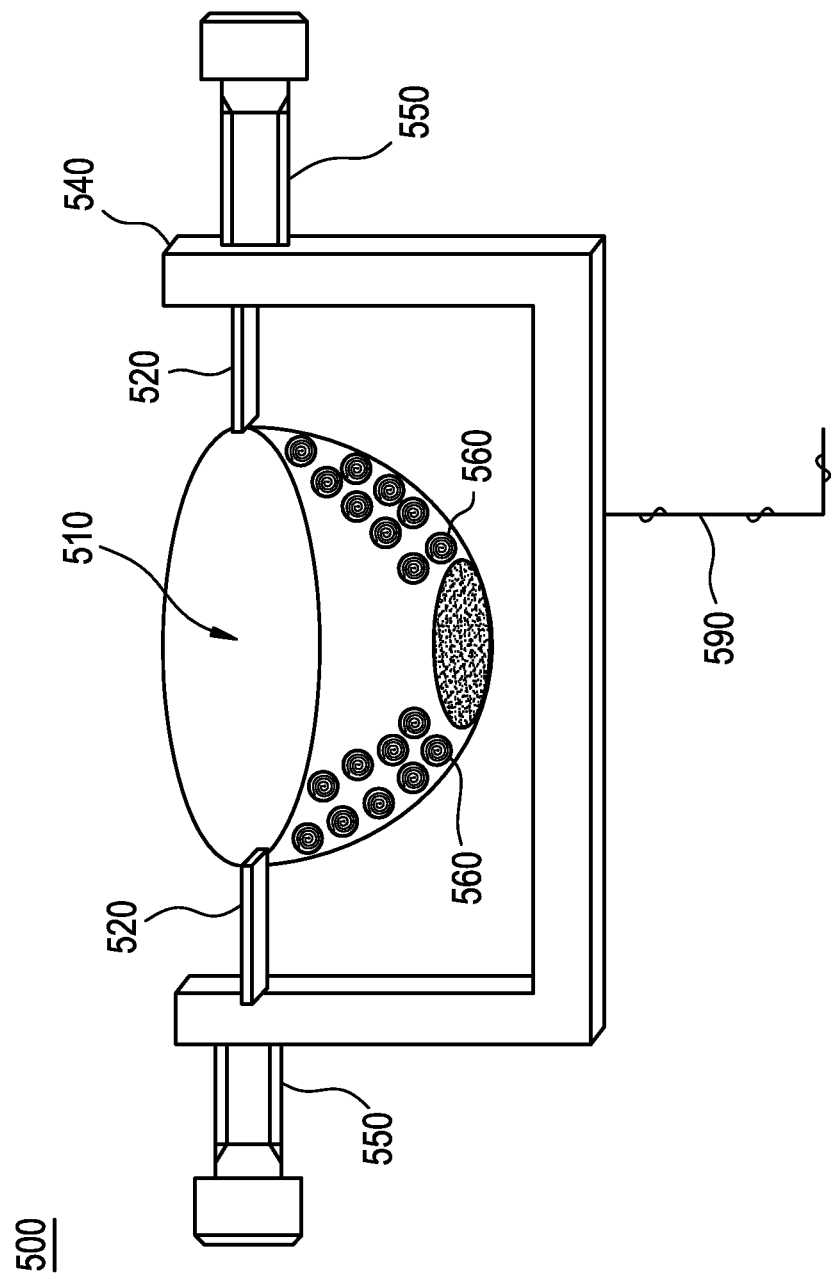
FIG. 5 is a planar view of an exemplary three-dimensional antenna mandrel implemented to interface with an antenna facing the convex side of the lens.
Figure 6:
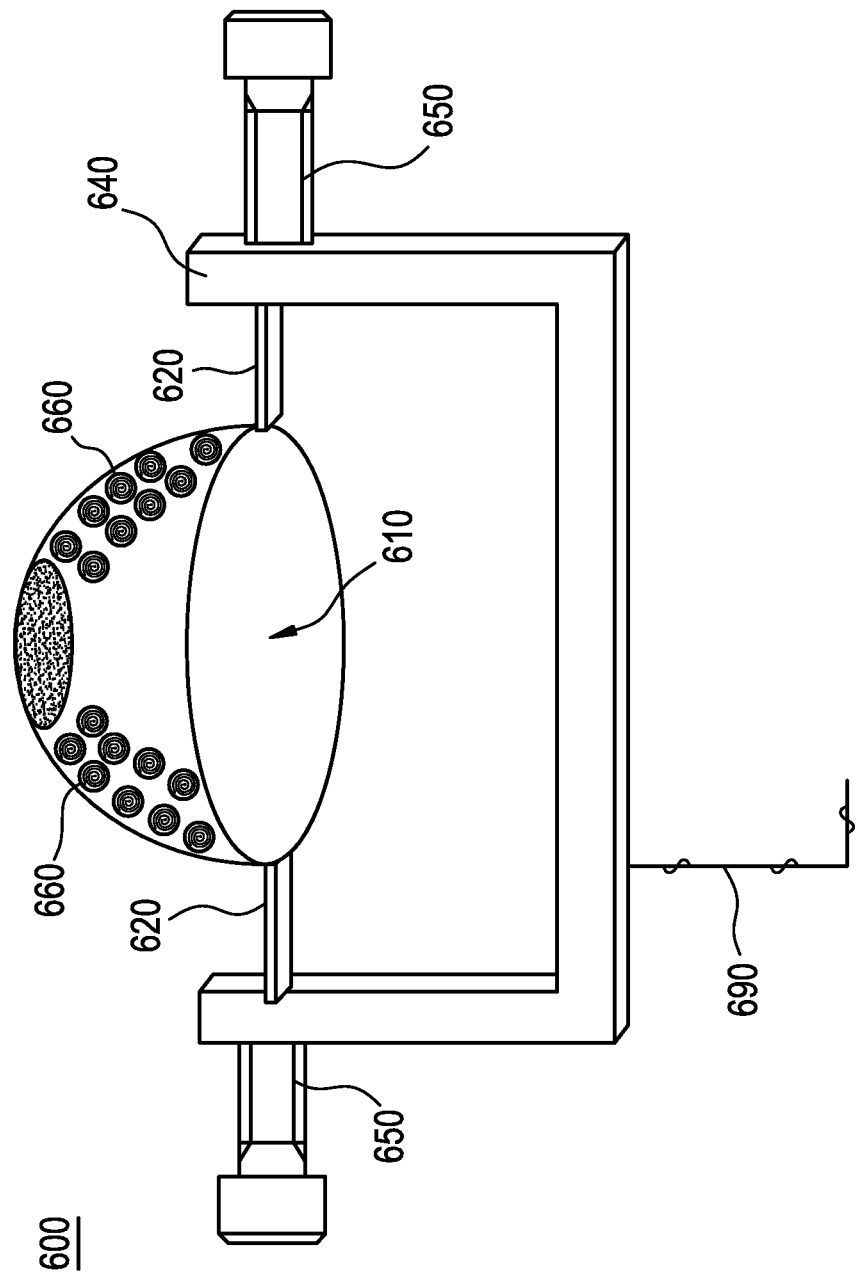
FIG. 6 is a planar view of an exemplary three-dimensional antenna mandrel implemented to interface with an antenna facing the concave side of the lens.

The radio transmitter system illustrated in FIG. 4 may be incorporated into a number of suitable devices including the exemplary embodiments of the devices illustrated in FIG. 5 through FIG. 8. As stated, the existence of inductive structures such as antennas, antenna assemblies and/or coils appropriate for use in an optical assembly, it is desirable to provide a convenient method for aligning the coil structure with an inductive coil structure for efficient near field coupling. FIG. 5 and FIG. 6 illustrate an exemplary embodiment of an antenna mandrel implemented to interface with an antenna facing either the concave or convex side of the lens. FIG. 5 illustrates an exemplary embodiment of the antenna mandrel implemented to interface with an antenna facing the concave side of the lens whereas FIG. 6 illustrates an exemplary embodiment of the antenna mandrel implemented to interface with an antenna facing the convex side of the lens. FIG. 7 illustrates an alternative exemplary embodiment of an antenna mandrel.

Referring now to FIG. 5, there is illustrated a side view of an exemplary three-dimensional antenna mandrel device comprising a radio transmitter system as illustrated in FIG. 4. As illustrated, the antenna mandrel device 500 comprises an antenna structure 510 which is held in place to a base 540 by one or more base support(s) 520. The base 540, the support 520, and mechanical actuators 550 may be formed from any suitable metal, ceramic or plastic suitable for housing the structure without interfering with the desired functionality. More specifically suitable radio frequency transmissive materials may include Tuff Span Fiberglass, Lexan XL-1 polycarbonate plastics, polystyrene boards and/or functionalized graphene nanoribbon films. As shown in this exemplary embodiment, the antenna structure 510 is formed to take the shape of a contact lens and oriented to interface with an antenna facing the concave side of the lens. However, antenna or antenna assemblies may be embedded in the ophthalmic device where the antenna coils may face the concave or convex side of the lens. Therefore, the antenna mandrel may be oriented to interface with an antenna facing the convex side of the ophthalmic device via one or more mechanical actuators 550, as illustrated in FIG. 6.

As illustrated in FIG. 5, the individual antennas 560 may be electronically interrogated by the radio transmitter system connected to the antenna mandrel via the connection cable 590 to determine which antenna is spatially aligned with the antenna in the ophthalmic device on the concave side of the lens.

Whereas FIG. 5 illustrates the exemplary embodiment of the antenna mandrel device implemented to interface with an antenna facing the concave side of the lens, FIG. 6 illustrates an exemplary embodiment of the antenna mandrel device implemented to interface with an antenna facing the convex side of the lens. As illustrated, the antenna mandrel device 600 comprises an antenna structure 610, which is held in place to a base 640 by one or more base support(s) 620. The base 640 and the base supports 620, and mechanical actuators 650 may be formed from any suitable metal, ceramic or plastic suitable for housing the mandrel without interfering with the desired functionality. More specifically suitable materials may include Tuff Span Fiberglass, Lexan XL-1 polycarbonate plastics, polystyrene boards and/or functionalized graphene nanoribbon films. The individual antennas 660 may be electronically interrogated by the radio transmitter system connected to the antenna mandrel via the connection cable 690 to determine which antenna is spatially aligned with the antenna in the ophthalmic device on the convex side of the lens.

As is known to one of ordinary skill in the art, antennas initiate communication when the internal antenna (antenna embedded in the ophthalmic device) and the external antenna (antenna on the antenna mandrel) are spatially aligned with each other. This configuration between the antennas permits all the field lines from one antenna coil to go into the field lines of the other antenna coil. It is important to note, the antenna embedded inside of an ophthalmic device ranges from less than 30 microns to more than 10 millimeters, which may increase the difficulty and efficiency upon which the spatial alignment may occur. However, the matrix of antennas 560, 660 on the antenna structure 510, 610 may accelerate this process due to the concentration of the antennas in the same geographical region that has been prescribed for the antenna embedded in the ophthalmic device. As mentioned previously, the antenna structure comprises a matrix of transmitter antenna coils embedded on a three-dimensional substrate in such a manner as to be concentrically aligned with the optic zone of a lens structure. In some embodiments, the antenna structures may be embedded in a three-dimensional dimensional substrate such as a flexible polymer, flexible polyimide film, ceramic films, flexible silicon- or silica-based substrates, polytetrafluoroethylene (PTFE), liquid crystal polymer (LCPS) or any other accommodating materials suitable for housing a matrix of antennas without impacting an ophthalmic device.

The radio transmitter system illustrated in FIG. 4 may be incorporated into the alternate exemplary three-dimensional antenna mandrel device as illustrated in side view in FIG. 7. The exemplary antenna mandrel device 700 comprises a base and/or frame 760 having one or more tiered, furcated connection cables 780, one or more antennas 790, and a radio transmitter system connection cable 715. The tiered, furcated connection cables 780 each comprise one or more branches which may be formed from multiple conductors that act as a pedestal for one or more antennas 790. In the preferred embodiment, the tiered furcated connection cables 780 extend to a rest point that allows the antenna 790 to be parallel with the base and/or frame 760. The base and/or frame 760 may be designed to allow the one or more connection cables 780 to rotate and move about one or more planes in three-dimensional space to scan the geographical region that has been prescribed for the antenna embedded in the ophthalmic device. In some embodiments the antenna mandrel device 700 may be configured to connect to a robotic vision system 735 via connection cable 740 to assist or facilitate the coarse-alignment. The antennas 790 may be electronically interrogated by the radio transmitter system connected to the antenna mandrel via the connection cable 715 to determine which antenna is spatially aligned with the antenna in the ophthalmic device.

Figure 8:
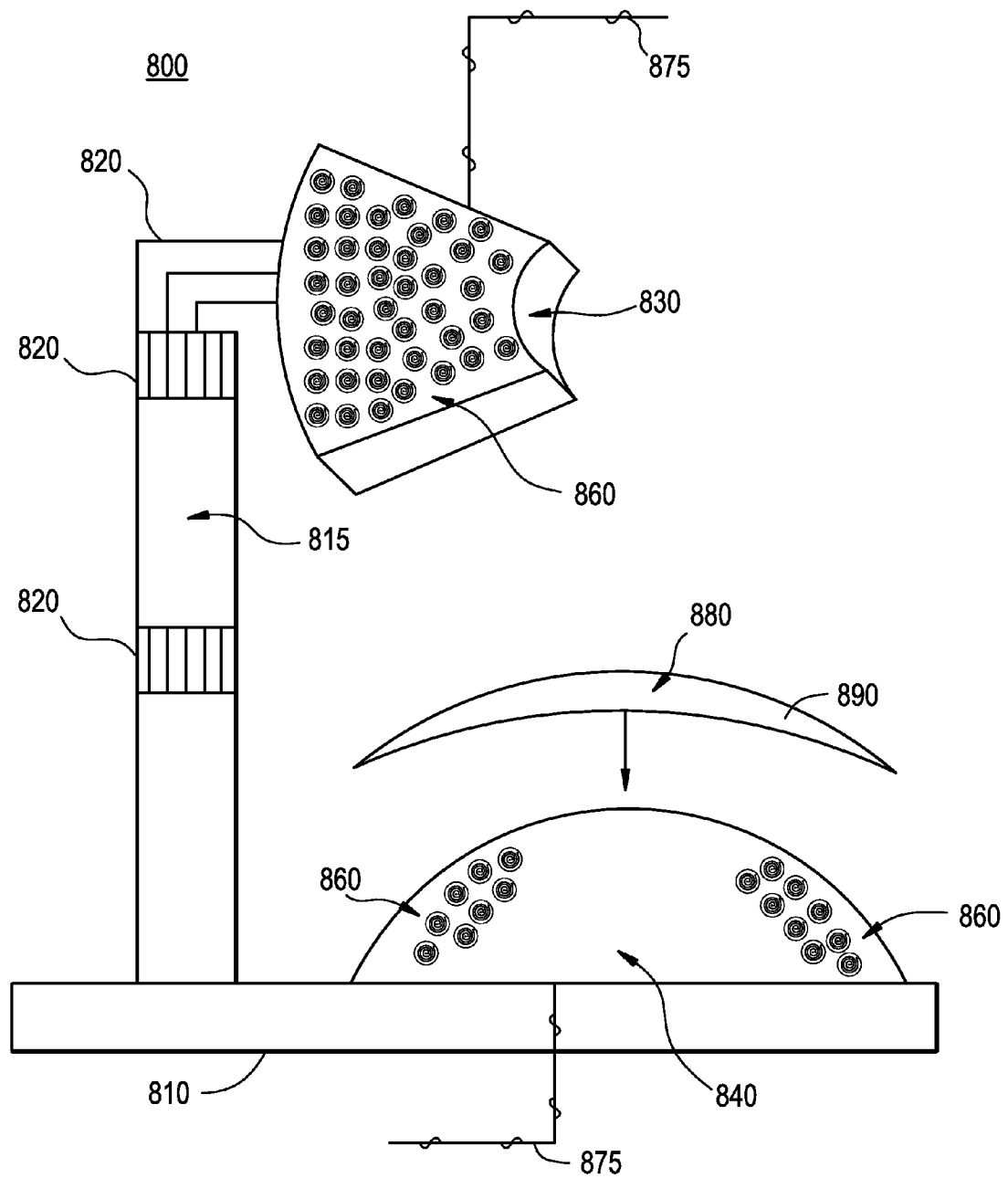
FIG. 8 illustrates a planar view of an alternative exemplary three-dimensional antenna mandrel implemented to interface with an antenna facing the concave side of the lens.

The radio transmitter system illustrated in FIG. 4 may be incorporated into the alternate exemplary antenna mandrel device as illustrated in side view in FIG. 8, which is implemented to interface with an antenna facing the concave side of the lens. Although the antenna mandrel device 800 is illustrated to interface with an antenna facing the concave side, the device may be configured to interface with an antenna facing the convex side of the lens. The exemplary antenna mandrel device 800 comprises a base 810, a ledger 815, a first substrate 840, and a second substrate 830. The ledger 815 further comprises one or more mechanical actuators 820, and the second substrate 830 configured for movement on, or rotation about one or more planes in a three-dimensional space in relation to the first substrate 840. The base 840, the ledger 815, and the one or more mechanical actuators 820 may be formed from any suitable metal, ceramic, or plastic suitable for housing the structure without interfering with the desired functionality. More specifically suitable radio frequency transmissive materials may include Tuff Span Fiberglass, Lexan XL-1 polycarbonate plastics, polystyrene boards and/or functionalized graphene nanoribbon films. As shown in this exemplary embodiment, the first substrate 840 is formed to take the shape of an ophthalmic device and oriented to interface with an antenna facing either the concave or convex side of the lens. In other exemplary embodiments, the first substrate 840 may be formed to hold the ophthalmic device 880 in a fixed position or to allow movement or rotation about one or more of planes in three-dimensional space in relation to the second substrate 830. The first substrate 840 and second substrate 830 may be formed from materials such as a flexible polymer, flexible polyimide film, ceramic films, flexible silicon- or silica-based substrates, polytetrafluoroethylene (PTFE), liquid crystal polymer (LCPS) or any other accommodating materials suitable for housing a matrix of antennas without impacting an ophthalmic device.

As shown in FIG. 8, the first substrate 830 and the second substrate 840 may have one or more arrays of submillimeter-sized antennas 860 embedded in a substantially annular arrangement. In other exemplary embodiments, either the first substrate 830 or the second substrate 840 will have one or more arrays of submillimeter-sized antennas 860 embedded in the same spatial region that has been prescribed for the antenna 890 embedded in the ophthalmic device 880; and further comprise the robotic vision system, as illustrated in FIG. 7. The robotic vision system 735 may be connected via the connection cables 875 to facilitate and expedite the coarse-alignment and the fine-tune alignment process. For example, the robotic vision system may be configured to move or rotate about one or more of the planes in three-dimensional space, in order to locate the submillimeter-sized antenna embedded in the ophthalmic device. In additional embodiments, the robotic vision system may be fixed and connected to a moveable base that rotates or moves about one or more planes in three-dimensional space to allow a vision system to fully scan the ophthalmic device for the submillimeter-sized antenna.

As described herein, the antennas may take on any number of forms, including traces on a circuit board, turns of wire embedded in the lens, printed on a circuit board, turns of wire embedded in the lens. Associated with the antennas are antenna related circuits.

Any antenna designed preferably is designed to work on-body and be embedded in a saline environment with limited area and volume available. Accordingly, small magnetic loop devices are preferred, as monopoles and dipoles as well as similar antennas are not good on-body or in saline.

The antennas set forth herein, as well as any other antenna design may be realized using a fractal design, as is known in the relevant art, to optimize performance, including size, efficiency, input impedance, bandwidth, and multiband usage. Essentially, a fractal antenna is any antenna structure that uses a fractal, self-similar design to maximize the length or increase the perimeter of a material that is able to transmit and/or receive electromagnetic radiation within a given total surface area or volume.

Antenna tuning units are generally not required for use with fractal antennas due to their wide bandwidth and complex resonance. As set forth herein and as it known in the art, antennas function by transmitting and/or receiving electromagnetic waves. There are a number of key factors which must be addressed in any antenna design and they include, gain, efficiency, impedance, bandwidth, polarization, directionality and radiation pattern. These factors are all important and can be varied depending on the application. For example, if an antenna is to be utilized in a contact lens, the antenna is preferably designed as a directional antenna with the bulk of radiated power travelling out of the eye and away from the head. Desired frequency and bandwidth may be selected or chosen depending on availability and desired functionality. Impedance, i.e. the voltage to current ratio at the input of the antenna may also be determined by the specific design.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An antenna array for electrically coupling with at least one sub-millimeter-sized antenna embedded in a biomedical device, the antenna array comprising:
   a base;
   a first substrate supported by the base, wherein the first substrate has a first shape configured to interface with a biomedical device having one or more shapes, one of which is complimentary to the first shape; and
   one or more arrays of isolated, submillimeter-sized antennas configured to provide optimized near-field coupling between at least one of the isolated, submillimeter-sized antennas in the one or more arrays and the at least one submillimeter-sized antenna in the biomedical device, wherein at least one of the one or more arrays of isolated, submillimeter-sized antennas and the biomedical device are movable relative to each other.

2. The antenna array according to claim 1, wherein the biomedical device comprises an ophthalmic device.

3. The antenna array according to claim 2, wherein the ophthalmic device comprises a contact lens.

4. The antenna array according to claim 3, wherein the contact lens further comprises an optic zone, a peripheral zone surrounding the optic zone, and a skirt zone surrounding the peripheral zone.

5. The antenna array according to claim 3, wherein the contact lens comprises a soft contact lens.

6. The antenna array according to claim 2, wherein the ophthalmic device comprises an intraocular lens.

7. The antenna array according to claim 2, wherein the ophthalmic device further comprises an optic zone, and a peripheral zone surrounding the optic zone.

8. The antenna array according to claim 1, wherein the base is configured for mechanical movement on one or more planes in three-dimensional space.

9. The antenna array according to claim 1, wherein the base is configured to be electrically steerable for movement on one or more planes in three-dimensional space.

10. The antenna array according to claim 1, wherein the base is configured to be fixed.

11. The antenna array according to claim 1, wherein the base is configured to connect to a robotic vision system.

12. The antenna array according to claim 11, wherein the robotic vision system is configured to coarse-align the one or more arrays of isolated, submillimeter-sized antennas with the one or more isolated, submillimeter-sized antenna in the biomedical device.

13. The antenna array according to claim 11, wherein the robotic vision system is configured to fine-align at least one antenna in the one or more arrays of isolated, submillimeter-sized antennas with the one or more isolated, submillimeter-sized antenna in the biomedical device.

14. The antenna array according to claim 11, wherein the robotic vision system is configured to be electrically steerable for movement on one or more planes in three-dimensional space.

15. The antenna array according to claim 1, wherein the first substrate is configured to rotate about one or more planes in three-dimensional space.

16. The antenna array according to claim 1, wherein the one or more arrays of isolated, submillimeter-sized antennas are embedded in the first substrate.

17. The antenna array according to claim 16, wherein the one or more arrays of isolated, submillimeter-sized antennas are embedded on the first substrate to extend to a region corresponding to a peripheral zone.

18. The antenna array according to claim 16, wherein the one or more arrays of isolated, submillimeter-sized antennas are embedded on the first substrate to extend to a region corresponding to a skirt zone of an ophthalmic device.

19. The antenna array according to claim 16, wherein the one or more arrays of isolated, submillimeter-sized antennas are embedded on the first substrate to extend to a region corresponding to an optic zone of an ophthalmic device.

20. The antenna array according to claim 16, wherein the one or more arrays of isolated, submillimeter-sized antennas are embedded on the first substrate to form a substantially annular arrangement.

21. The antenna array according to claim 1, wherein the first substrate comprises a polymer.

22. The antenna array according to claim 1, wherein the first substrate comprises a polyimide film.

23. The antenna array according to claim 1, wherein the first substrate comprises a silicon-based substrate.

24. The antenna array according to claim 1, wherein the first substrate comprises a silica-based substrate.

25. The antenna array according to claim 1, wherein the first substrate comprises polytetrafluoroethylene.

26. The antenna array according to claim 1, wherein the first substrate comprises liquid crystal polymer.

27. The antenna array according to claim 1, wherein the antenna array further comprises a ledger.

28. The antenna array according to claim 27, wherein the ledger further comprises one or more mechanical actuators.

29. The antenna array according to claim 28, wherein the one or more mechanical actuators are configured to rotate about one or more planes in three-dimensional space.

30. The antenna array according to claim 28, wherein the one or more mechanical actuators are configured for movement on one or more planes in three-dimensional space.

31. The antenna array according to claim 1, wherein the antenna array further comprises a second substrate.

32. The antenna array according to claim 31, wherein the second substrate is affixed to at least one of the one or more mechanical actuators.

33. The antenna array according to claim 32, wherein the one or more mechanical actuators affixed to the second substrate is configured to rotate about one or more planes in three-dimensional space.

34. The antenna array according to claim 31, wherein the one or more arrays of isolated, submillimeter-sized antennas are embedded in the second substrate.

35. The antenna array according to claim 34, wherein the one or more arrays of isolated, submillimeter-sized antennas are embedded on the second substrate to extend to a region corresponding to a peripheral zone.

36. The antenna array according to claim 34, wherein the one or more arrays of isolated, submillimeter-sized antennas are embedded on the second substrate to extend to a region corresponding to a skirt zone of an ophthalmic device.

37. The antenna array according to claim 34, wherein the one or more arrays of isolated, submillimeter-sized antennas are embedded on the second substrate to extend to a region corresponding to an optic zone of an ophthalmic device.

38. The antenna array according to claim 34, wherein the one or more arrays of isolated, submillimeter-sized antennas are embedded on the second substrate to form a substantially annular arrangement.

39. The antenna array according to claim 31, wherein the second substrate is configured for movement on one or more planes in three-dimensional space.

40. The antenna array according to claim 31, wherein the second substrate comprises a polymer.

41. The antenna array according to claim 31, wherein the second substrate comprises a polyimide film.

42. The antenna array according to claim 31, wherein the second substrate comprises a silicon-based substrate.

43. The antenna array according to claim 31, wherein the second substrate comprises a silica-based substrate.

44. The antenna array according to claim 31, wherein the second substrate comprises polytetrafluoroethylene.

45. The antenna array according to claim 31, wherein the second substrate comprises liquid crystal polymer.

46. The antenna array according to claim 1, wherein the antenna array further comprises one or more tiered, furcated connection cables.

47. The antenna array according to claim 46, wherein the one or more tiered, furcated connection cables are configured to be electrically steerable.

48. The antenna array according to claim 46, wherein the one or more arrays of isolated, submillimeter-sized antennas are connected to the one or more tiered, furcated connection cables.

49. The antenna array according to claim 46, wherein the one or more tiered, furcated connection cables are enclosed in the ledger.

50. The antenna array according to claim 1, wherein the one or more arrays of isolated, submillimeter-sized antennas comprise one or more arrays of isolated, single-turn submillimeter-sized loop antennas.

51. The antenna array according to claim 50, wherein the one or more arrays of isolated, submillimeter-sized antennas comprise conductive coil wires.

52. The antenna array according to claim 1, wherein the one or more arrays of isolated, submillimeter-sized antennas comprise one or more arrays of isolated multi-turn submillimeter-sized loop antennas.

53. The antenna array according to claim 52, wherein the one or more arrays of isolated multi-turn submillimeter-sized antennas comprise conductive wire coils.

54. The antenna array according to claim 1, wherein the one or more arrays of isolated, submillimeter-sized antennas comprise one or more arrays of isolated spiral submillimeter-sized antennas.

55. The antenna array according to claim 54, wherein the one or more arrays of isolated spiral submillimeter-sized antennas comprise conductive wire coils.

56. The antenna array according to claim 1, wherein the one or more arrays of isolated, submillimeter-sized antennas further comprise one or more electrical interconnects.

* * * * *